(12) United States Patent
Medema et al.

(10) Patent No.: US 10,213,303 B2
(45) Date of Patent: *Feb. 26, 2019

(54) RAPID DEPLOYMENT ARTIFICIAL CHORDAE TENDINAE SYSTEM

(71) Applicant: ON-X LIFE TECHNOLOGIES, INC., Austin, TX (US)

(72) Inventors: Ryan Medema, Pflugerville, TX (US); Mark Seeley, Austin, TX (US)

(73) Assignee: On-X Life Technologies, Inc., Austin, TX (US)

( * ) Notice: Subject to any disclaimer, the term of this patent is extended or adjusted under 35 U.S.C. 154(b) by 289 days.

This patent is subject to a terminal disclaimer.

(21) Appl. No.: 15/334,888

(22) Filed: Oct. 26, 2016

(65) Prior Publication Data

US 2017/0105838 A1    Apr. 20, 2017

Related U.S. Application Data

(63) Continuation of application No. 15/013,612, filed on Feb. 2, 2016, now Pat. No. 9,480,565.
(Continued)

(51) Int. Cl.
*A61F 2/24* (2006.01)
*A61B 17/04* (2006.01)
(Continued)

(52) U.S. Cl.
CPC ........ *A61F 2/2457* (2013.01); *A61B 17/0401* (2013.01); *A61B 17/06066* (2013.01);
(Continued)

(58) Field of Classification Search
CPC ................. A61F 2/2457; A61F 2/2454; A61F 2002/304411; A61F 2220/0041;
(Continued)

(56) References Cited

U.S. PATENT DOCUMENTS 5,307,924 A    5/1994    Manosalva
5,391,182 A    2/1995    Chin
(Continued)

FOREIGN PATENT DOCUMENTS

AU    2015200387 A1    2/2015
CA       2369641 C      2/2009
(Continued)

OTHER PUBLICATIONS

Wikipedia, "Treasury Tag," http://en.wikipedia.org/wiki/Treasury_tag, Jan. 30, 2015, 2 pages.
(Continued)

*Primary Examiner* — David C Eastwood
(74) *Attorney, Agent, or Firm* — Trop, Pruner & Hu, P.C.

(57) ABSTRACT

An embodiment includes an apparatus comprising: a hollow needle with a narrowed inner diameter in a distal third of the needle; and a flexible chord coupled to proximal and distal conduits; wherein the distal conduit is in the needle and distal to the narrowed inner diameter and the proximal conduit is in the needle and proximal to the narrowed inner diameter; wherein: (a)(i) long axes of the proximal and distal conduits are substantially parallel to a long axis of the needle when the proximal and distal conduits are in the needle, and (a)(ii) the proximal and distal conduits are configured to rotate when deployed from the needle such that their long axes are not parallel to a long axis of the chord when the chord is fully extended. Other embodiments are described herein.

20 Claims, 11 Drawing Sheets

Related U.S. Application Data

(60) Provisional application No. 62/110,666, filed on Feb. 2, 2015, provisional application No. 62/237,880, filed on Oct. 6, 2015.

(51) Int. Cl.
  *A61B 17/06* (2006.01)
  *A61B 17/00* (2006.01)

(52) U.S. Cl.
  CPC ...... *A61B 17/06166* (2013.01); *A61F 2/2466* (2013.01); *A61B 2017/00539* (2013.01); *A61B 2017/00946* (2013.01); *A61B 2017/042* (2013.01); *A61B 2017/0406* (2013.01); *A61B 2017/0409* (2013.01); *A61B 2017/0417* (2013.01); *A61B 2017/061* (2013.01); *A61B 2017/0619* (2013.01); *A61B 2017/06052* (2013.01); *A61F 2210/0014* (2013.01); *A61F 2250/0007* (2013.01)

(58) Field of Classification Search
  CPC ............. A61F 2/08111; A61B 17/0487; A61B 17/04011; A61B 2017/00575; A61B 17/10; A61B 2017/0409; A61B 2017/0408; A61B 2017/0416; A61B 2017/0417; A61B 2017/042; A61B 2017/04221; A61B 2017/04241; A61B 17/04661; A61B 2017/0454
  See application file for complete search history.

(56) References Cited

U.S. PATENT DOCUMENTS

| | | |
|---|---|---|
| 5,431,666 A | 7/1995 | Sauer |
| 6,010,531 A | 1/2000 | Donlon |
| 6,797,002 B2 | 9/2004 | Spence |
| 6,869,444 B2 | 3/2005 | Gabbay |
| 6,945,996 B2 | 9/2005 | Sedransk |
| 6,966,916 B2 | 11/2005 | Kumar |
| 6,997,950 B2 | 2/2006 | Chawla |
| 7,241,257 B1 | 7/2007 | Ainsworth |
| 7,635,386 B1 | 12/2009 | Gammie |
| 7,645,286 B2 | 1/2010 | Catanese |
| 7,758,594 B2 | 7/2010 | Lamson |
| 7,766,923 B2 | 8/2010 | Catanese |
| 7,871,368 B2 | 1/2011 | Zollinger |
| 7,871,433 B2 | 1/2011 | Lattouf |
| 7,905,889 B2 | 3/2011 | Catanese |
| 7,951,158 B2 | 5/2011 | Catanese |
| 8,007,503 B2 | 8/2011 | Catanese |
| 8,157,719 B1 | 4/2012 | Ainsworth |
| 8,157,815 B2 | 4/2012 | Catanese |
| 8,216,254 B2 | 7/2012 | Lamson |
| 8,292,884 B2 | 10/2012 | Levine |
| 8,303,622 B2 | 11/2012 | Alkhatib |
| 8,323,336 B2 | 12/2012 | Hill |
| 8,333,776 B2 | 12/2012 | McLean |
| 8,343,187 B2 | 1/2013 | Cheng |
| 8,394,110 B2 | 3/2013 | Catanese |
| 8,425,535 B2 | 4/2013 | McLean |
| 8,439,969 B2 | 5/2013 | Gillinov |
| 8,500,800 B2 | 8/2013 | Maisano |
| 8,545,551 B2 | 10/2013 | Loulmet |
| 8,545,553 B2 | 10/2013 | Zipory |
| 8,663,243 B2 | 3/2014 | Lamson |
| 8,715,239 B2 | 5/2014 | Lamson |
| 8,715,298 B2 | 5/2014 | Catanese |
| 8,758,393 B2 | 6/2014 | Zentgraf |
| 8,778,016 B2 | 7/2014 | Janovsky |
| 8,900,252 B2 | 12/2014 | Lamson |
| 8,936,609 B2 | 1/2015 | Catanese |
| 8,939,996 B2 | 1/2015 | Cheng |
| 9,060,858 B2 | 6/2015 | Thornton |
| 2002/0019649 A1 | 1/2002 | Sikora |
| 2002/0068849 A1 | 6/2002 | Schweich |
| 2002/0188170 A1 | 12/2002 | Santamore |
| 2003/0105519 A1 | 6/2003 | Fasol |
| 2004/0073301 A1 | 4/2004 | Donlon |
| 2004/0093023 A1 | 5/2004 | Allen |
| 2005/0038509 A1 | 2/2005 | Ashe |
| 2005/0277966 A1 | 12/2005 | Ewers |
| 2005/0277981 A1 | 12/2005 | Maahs |
| 2006/0030885 A1 | 2/2006 | Hyde |
| 2006/0287716 A1 | 12/2006 | Banbury |
| 2007/0049952 A1 | 3/2007 | Weiss |
| 2007/0051377 A1 | 3/2007 | Douk |
| 2007/0073316 A1 | 3/2007 | Sgro |
| 2007/0100375 A1 | 5/2007 | Mikkaichi |
| 2007/0112338 A1 | 5/2007 | Cohen |
| 2007/0112385 A1 | 5/2007 | Conlon |
| 2007/0118151 A1 | 5/2007 | Davidson |
| 2007/0118213 A1 | 5/2007 | Loulmet |
| 2008/0195126 A1 | 8/2008 | Solem |
| 2008/0208219 A1 | 8/2008 | Suzuki |
| 2008/0228223 A1 | 9/2008 | Alkhatib |
| 2008/0228272 A1 | 9/2008 | Moaddeb |
| 2009/0043381 A1 | 2/2009 | Macoviak |
| 2009/0088837 A1 | 4/2009 | Gillinov |
| 2009/0177274 A1 | 7/2009 | Scorsin |
| 2009/0182192 A1 | 7/2009 | Shiono |
| 2010/0023118 A1 | 1/2010 | Medlock |
| 2010/0042147 A1 | 2/2010 | Janovsky |
| 2010/0179574 A1 | 7/2010 | Longoria |
| 2010/0249919 A1 | 9/2010 | Gillinov |
| 2011/0011917 A1 | 1/2011 | Loulmet |
| 2011/0060407 A1 | 3/2011 | Ketai |
| 2013/0006352 A1 | 1/2013 | Yaron |
| 2013/0096673 A1 | 4/2013 | Hill |
| 2013/0110230 A1 | 5/2013 | Solem |
| 2013/0282059 A1 | 10/2013 | Ketai |
| 2014/0114404 A1 | 4/2014 | Gammie |
| 2014/0142689 A1 | 5/2014 | DeCanniere |
| 2014/0364938 A1 | 12/2014 | Longoria |

FOREIGN PATENT DOCUMENTS

| | | |
|---|---|---|
| EP | 2023822 A2 | 2/2009 |
| EP | 2741711 A2 | 6/2014 |
| WO | 2012040865 A1 | 4/2012 |
| WO | 2012137208 A1 | 10/2012 |
| WO | 2014028725 A1 | 2/2014 |
| WO | 2014093861 A1 | 6/2014 |

OTHER PUBLICATIONS

Uline, "Long Needle Price Tag Gun / Fasteners," Online Catalog, http://www.uline.com/BL_476/Long-Needle-Price-Tag-Gun-Fasteners, Jan. 23, 2015, 1 page.

Hongyu Plastic String Co., Limited, "Elastic Rope With Metal Tipping/Elastic Treasury Tag," Online Catalog, http://hysjsd.en.alibaba.com/productlist.html, Jan. 30, 2015, 4 pages.

Kendall, "Fixation Device ProTack Pistol Grip 30 Titanium Helical Fasteners," Supreme Med, Mnf #: 174006, http://www.suprememed.com/fixation-device-protack-pistol-grip-30-titanium-helicalfasteners-152138, Feb. 1, 2016, 1 page.

"Ti-KNOT® Device: Features," LSI Solutions®, Isisolutions.com, Dec. 23, 2009, https://web.archive.org/web/20091223024458/http://www.Isisolutions.com/tkfeatures, 2 pages.

Seeburger, et al., "Trans-apical beating-heart implantation of neo-chordae to mitral valve leaflets: results of an cute animal study," European Journal of Cardio-Thoracic Surgery 41.1 (2012): 4 pages.

Farndons Limited, "Solutions," Catalog, http://www.famdons.com/flipbook/Farndons-Catalogue-2015/files/assets/common/downloads/Farndons-Retail-Catalogue-2012.pdf, Feb. 1, 2016, 7 pages.

Smallbusinesssupplies.net, "Products: Standard Tag-It 2 Barbs," Small Business Supplies, http://www.smallbusinesssupplies.net/tagging-guns-supplies.

Salvador, et al., "A 20-year experience with mitral valve repair with artificial chordae in 608 patients," The Journal of Thoracic and Cardiovascular Surgery 135.6 (2008), 9 pages.

(56) References Cited

OTHER PUBLICATIONS

Bajona, et al., "Beating-heart, off-pump mitral valve repair by implantation of artificial chordae tendineae: an acute in vivo animal study," The Journal of thoracic and cardiovascular surgery 137.1 (2009), 6 pages.

Bajona, et al., "Tension measurement of artificial chordae tendinae implanted between the anterior mitral valve leaflet and the left ventricular apex: an in vitro study," Innovations: Technology and Techniques in Cardiothoracic and Vascular Surgery 3.1 (2008), 5 pages.

Ionescu, et al., "Autologous fascia lata for heart valve replacement," Thorax 25.1 (1970), 11 pages.

Ionescu, et al., "Mitral valve replacement with aortic heterografts in humans," Thorax 22.4 (1967), 10 pages.

Chiappini, et al., "Replacement of chordae tendineae with polytetrafluoroethylene (PTFE) sutures in mitral valve repair: early and long-term results," Journal of Heart Valve Disease 15.5 (2006), 7 pages.

Erickson, Ben, "Testing Wall Anchors and Picture Hangers," todayshomeowner.com, 2008, 8 pages.

International Searching Authority, "Notification of Transmittal of the International Search Report and the Written Opinion of the International Searching Authority," dated May 16, 2016 in International application No. PCT/US2016/016156.

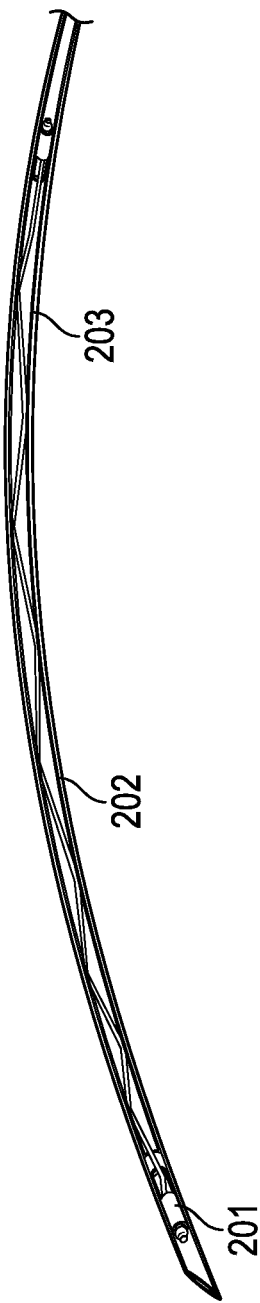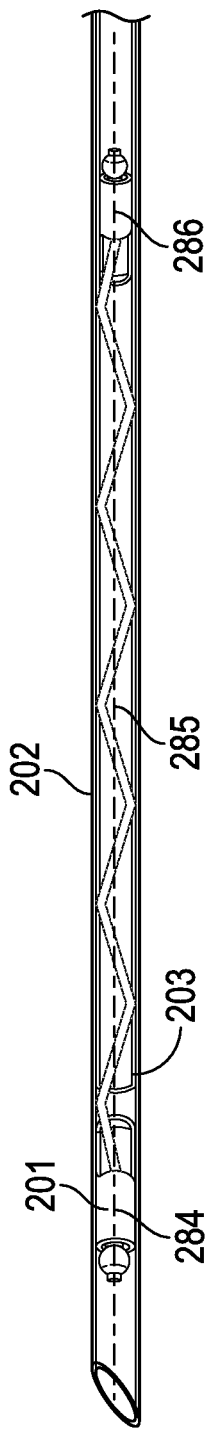
FIG.2A
FIG.2B

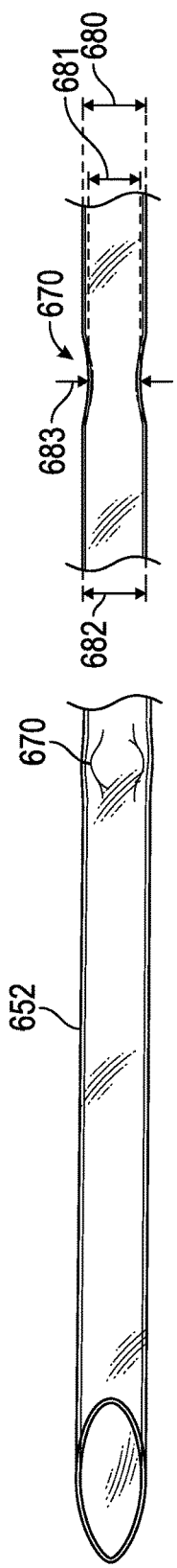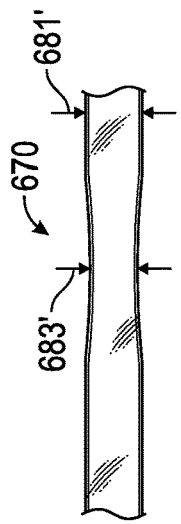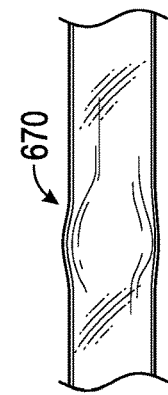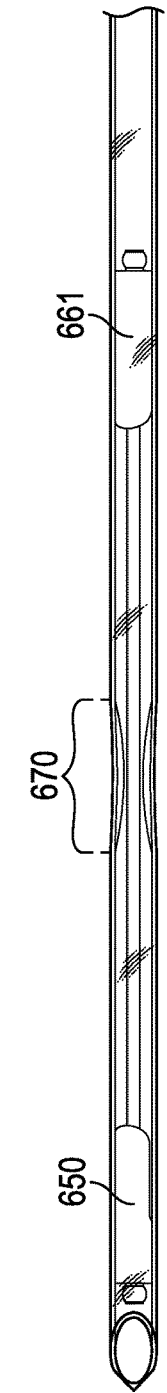
FIG. 7A  FIG. 7B  FIG. 7C  FIG. 7D  FIG. 7E

FIG. 8E    870
870
FIG. 8F
FIG. 8G    870

RAPID DEPLOYMENT ARTIFICIAL CHORDAE TENDINAE SYSTEM

CROSS-REFERENCE TO RELATED APPLICATIONS

This application is a continuation of U.S. patent application Ser. No. 15/013,612 filed on Feb. 2, 2016 and entitled "Rapid Deployment Artificial Chordae Tendinae System," which claims priority to both (a) U.S. Provisional Patent Application No. 62/110,666 filed on Feb. 2, 2015 and entitled "Rapid Deployment Artificial Chordae Tendinae System" and (b) U.S. Provisional Patent Application No. 62/237,880 filed on Oct. 6, 2015 and entitled "Rapid Deployment Artificial Chordae Tendinae System". The content of each of the above applications is hereby incorporated by reference.

TECHNICAL FIELD

Embodiments of the invention are in the field of cardiology-related medical devices.

BACKGROUND

Mitral valve prolapse is a significant cause of cardiovascular morbidity and mortality. As a result, surgical intervention is often required. As one of the surgical options currently available, mitral valve repair is well established and is applicable in patients with mitral valve prolapse due to degenerative mitral-valve disease. The techniques of mitral valve repair include inserting a cloth-covered ring around the valve to bring the leaflets into contact with each other (annuloplasty), removal of redundant/loose segments of the leaflets (quadrangular resection), and re-suspension of the leaflets with artificial chordae (chordal replacement).

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

FIGS. 2(a)-2(b) show angled and non-angle needles in embodiments of the invention.

FIGS. 7(a)-7(e) illustrate various aspects of a crimped needle embodiment of the invention.

FIGS. 8(a)-8(g) illustrate various stages of deployment of a crimped needle embodiment of the invention.

DETAILED DESCRIPTION

Figure 1A:
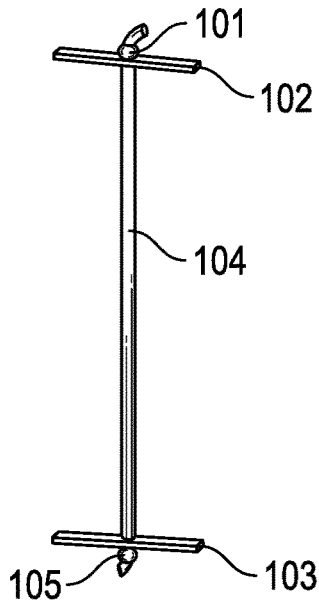
FIGS. 1(a)-1(f) depict varying chordae structures in embodiments of the invention.

In the following description, numerous specific details are set forth but embodiments of the invention may be practiced without these specific details. Well-known structures and techniques have not been shown in detail to avoid obscuring an understanding of this description. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner "Connected" may indicate elements are in direct physical or electrical contact with each other and "coupled" may indicate elements co-operate or interact with each other, but they may or may not be in direct physical or electrical contact. Also, while similar or same numbers may be used to designate same or similar parts in different figures, doing so does not mean all figures including similar or same numbers constitute a single or same embodiment.

Regarding chordal replacement addressed above, replacement of diseased mitral valve chordae with expanded polytetrafluoroethylene (ePTFE) sutures is an established technique with good long-term results. Various techniques have been described to assist the surgeon to establish the correct replacement chordal length. However, despite the surgical challenges of attaching the ePTFE suture to papillary muscles and determining the correct length for artificial chordae, few effective products have been developed to assist surgeons with this challenging procedure. In general, surgical approaches have centered on individual surgeon-based techniques including the use of a small tourniquet or weaving the suture through the leaflet to the mitral annulus and thereafter readjusting the length while the ventricle is filled under pressure. Applicant has noted how these varying techniques lead to inconsistencies and varying levels of clinical success.

An embodiment includes a combination prosthesis and attachment/delivery device or system, which allows a surgeon to quickly implant prefabricated artificial chordae Tendinae prosthesis (e.g., to repair mitral valve regurgitation or prolapse). The embodiment allows the surgeon to, for example, click a trigger and fully deploy the implant, completely or almost completely eliminating the need for the surgeon to tie complicated and time-consuming knot bundles, or crimp additional components to secure the prosthesis (as is the case with conventional crimping systems). Finally, embodiments allow for minimally invasive (e.g., through a space between a patient's ribs) and transcatheter deployment of the prosthesis, ultimately enabling quicker procedures and better patient outcomes.

An embodiment includes a combination prosthesis and attachment/delivery device or system, which allows a surgeon to quickly implant prefabricated artificial chordae Tendinae prosthesis (e.g., to repair mitral valve regurgitation or prolapse). The embodiment allows the surgeon to, for example, fully deploy the implant using fluid pressure (e.g., saline), completely or almost completely eliminating the need for the surgeon to tie complicated and time-consuming knot bundles, or crimp additional components to secure the prosthesis (as is the case with conventional crimping systems). Finally, the embodiment allows for minimally invasive and trans-catheter deployment of the prosthesis, ultimately enabling quicker procedures and better patient outcomes.

Embodiments address various problems found in conventional systems. For example, conventional techniques and products require the surgeon to take a much larger role in the surgery. For example, the surgeon must fabricate suture loops and then position, install, and adjust the loops and finally tie a series of knots to secure the prosthesis. In contrast, an embodiment is a rapid deployment system that requires significantly less of the surgeon and dramatically shortens the duration of the surgery.

Embodiments of the invention addressed herein include various apparatuses, systems, and surgical techniques.

FIGS. 1(a)-1(f) depict varying chordae structures in embodiments of the invention. FIGS. 1(g)-1(h) depict the embodiment of FIG. 1(e) during different stages of its deployment.

Figure 1B:
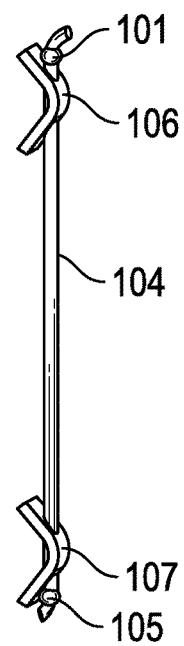
Figure 1C:
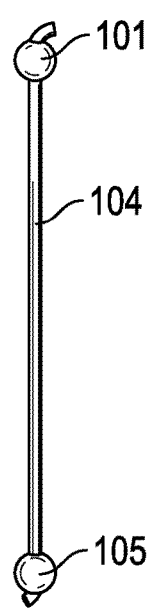
Figure 1D:
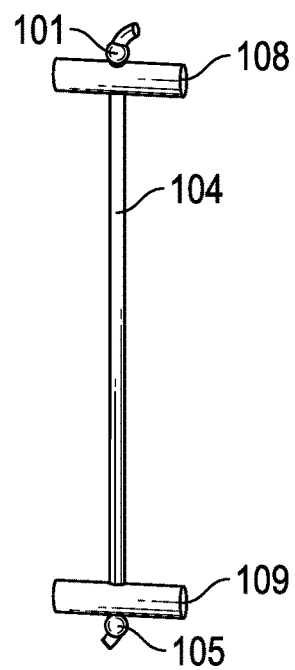
Figure 1E:
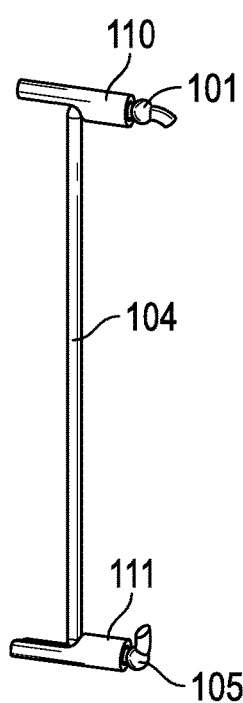
Figure 1F:
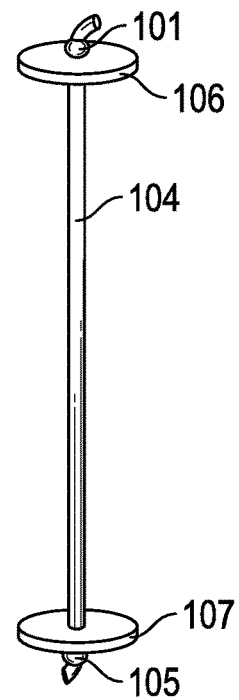
Figure 1G:
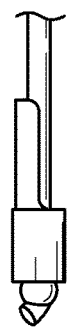
FIGS. 1(g)-1(h) depict the embodiment of FIG. 1(e) during different stages of its deployment.
Figure 1H:
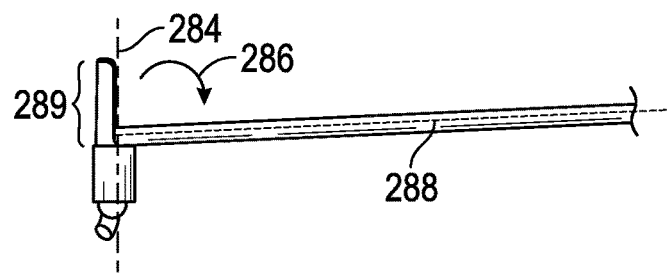

FIG. 1(a) includes mechanical knots or melted ePTFE sutures 101, 105, PTFE strips 102, 103, and ePTFE suture 104. FIG. 1(b) includes components similar to FIG. 1(a) but further adds PTFE felt pledgets 106, 107 in place of the PTFE strips of FIG. 1(a). FIG. 1(f) is similar to FIG. 1(b) but includes pledgets shaped differently from those of FIG. 1(b). FIG. 1(c) is similar to FIG. 1(a) but foregoes PTFE strips or pledgets and instead relies on knots 101, 105 being enlarged and configured to compress within a delivery conduit (e.g., needle) but then expand to offer secure purchase to leaflet or papillary tissue. FIG. 1(d) includes components similar to FIG. 1(a) but further adds thickened ePTFE suture portions 108, 109 in place of the PTFE strips of FIG. 1(a). FIG. 1(e) includes components similar to FIG. 1(a) but further adds slotted ePTFE tubes 110, 111 in place of the PTFE strips of FIG. 1(a). The slotted tube embodiment of FIG. 1(e) offers a small cross sectional diameter (when collapsed, such as FIG. 1(g)) while still offering a broad and reliable anchoring feature (once deployed, such as FIG. 1(h)). The slotted tube is sometimes referred to herein as a "ferrule" or some form of conduit (a pipe or tube or trough through which something (such as suture) passes).

Embodiments of FIGS. 1(a)-1(f) feature a premeasured length of ePTFE 104 and a method of capping both ends of the construct with PTFE and/or ePTFE components (which may be rigid in some embodiments). ePTFE and PTFE have excellent biocompatibility, resistance to degradation, flexibility, and a long clinical history of use. Each of these assemblies comprises artificial mitral chordae tendinae prosthesis.

FIGS. 2(a)-2(b) respectively show angled and non-angle needles in embodiments of the invention. Each figure includes prosthesis 201. Prosthesis 201 (e.g., conduit) is collapsed and nested within the long needle 202. Distal fluke 201 has a shoulder such that the ramrod 203 (only shown in FIG. 2(b)) may deploy the prosthesis. Needle 202 houses prosthesis 201 and ramrod 203 and pierces cardiac tissue. Needle 202 may be straight (FIG. 2(b)), curved (FIG. 2(a)), and/or malleable (to be made straight or curved) allowing the surgeon to choose the appropriate geometry. Materials for the needle are thin walled stainless steel or nitinol tubing in several embodiments Ramrod 203 deploys the prosthesis when actuated. Ramrod 203 is, in an embodiment, hollow and flexible to follow the geometry of the needle, and is concentric to the prosthesis and the long needle. Ramrod 203 pushes on a shoulder or other appendage or projection or recess or surface of distal fluke 201. Materials for the ram rod are thin walled stainless steel or nitinol tubing in embodiments. A device handle or actuation mechanism (not pictured) allows the surgeon to position and direct the needle into the cardiac tissue, and to deploy the prosthesis when desired. In an embodiment the prosthesis is preconfigured with an attachment device (e.g., chord is already located within needle along with, some embodiments, the ramrod), and delivered sterile to the surgeon. An embodiment is single use disposable.

FIGS. 3(a)-3(f) show various stages of deployment in a process of an embodiment of the invention. Regarding the process, in Step 1 the surgeon measures the desired length for artificial chordae tendinae, and chooses an attachment device that is preconfigured with a prosthesis of corresponding length. In Step 2 the surgeon pierces the mitral leaflet at the desired location (for chordal repair) with the distal tip of the attachment device (FIG. 3(a)). In Step 3 the surgeon pierces the papillary muscle at the desired location (for chordal repair) with the distal tip of the attachment device (FIG. 3(b)). In Step 4 the surgeon actuates the attachment device (e.g., deploys trigger that advances ramrod or manually pushes on ramrod), which advances the ramrod and deploys the distal end of the prosthesis at the far side of the papillary muscle (FIG. 3(c)). In Step 5 the surgeon retracts the attachment device out of the papillary muscle. A fluke 311 on the distal end of the prosthesis engages the papillary tissue 312 (rotates into position) and prevents the prosthesis from backing out (FIG. 3(d)). In Step 6 the surgeon continues to retract the attachment device beyond the leaflet 313 (FIG. 3(e)). Once attachment device clears the leaflet, it is discarded. In Step 7 the surgeon tests valve coaptation with the prosthesis by pressurizing the ventricle with saline. A flukes on the proximal end of the prosthesis engages the leaflet (rotates into position) and prevents prosthesis back out (FIG. 3(f)). The surgeon may implant additional prostheses if additional chords are desired.

Figure 4A:
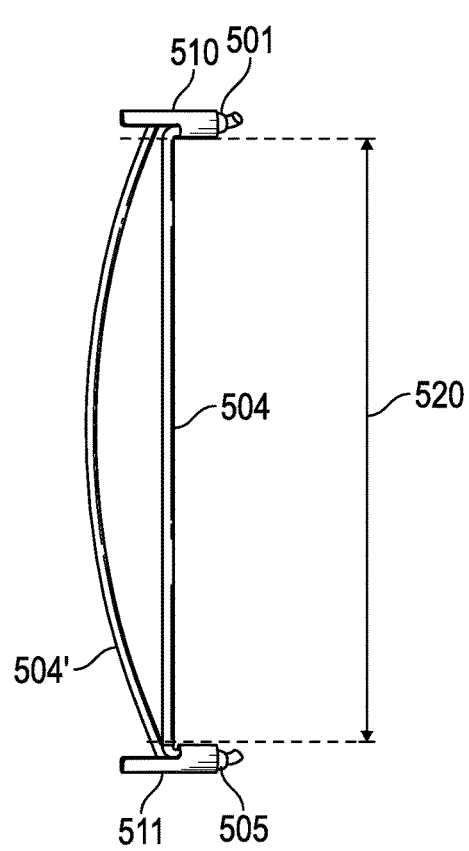
FIGS. 4(a)-4(b) show varying length stages of an adjustable length embodiment of the invention.
Figure 4B:
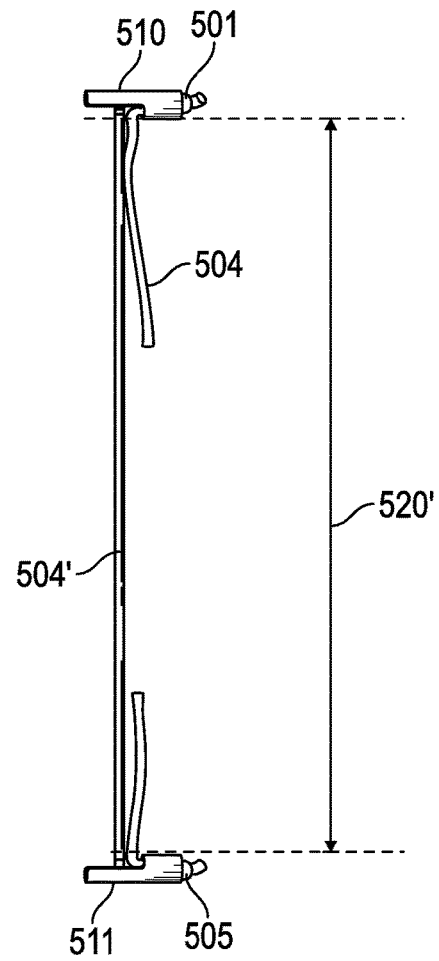

FIGS. 4(a)-4(c) shows varying length stages of an adjustable length embodiment of the invention. In FIG. 4(a) ePTFE suture segments 501, 505 are knotted, welded, or bonded together outside of flukes. Any of the prosthesis designs from the previous figures (e.g., FIGS. 1(a)-1(f)) can be fabricated into adjustable constructs by including one (or more) additional ePTFE suture strands 504' which are slightly longer than a first strand 504. With these concepts, the surgeon may cut the short ePTFE segment to extend the artificial chord prosthesis overall by some pre-determined fixed length (Δ) (the different between length 520 and 520'). Adjustment is performed after implantation, based on saline testing.

Figure 5A:
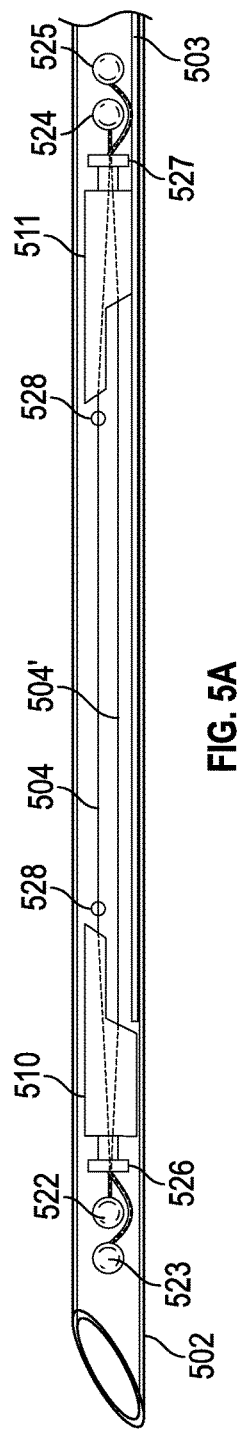
FIG. 5(a) shows a multi-chord embodiment of the invention.
Figure 5B:
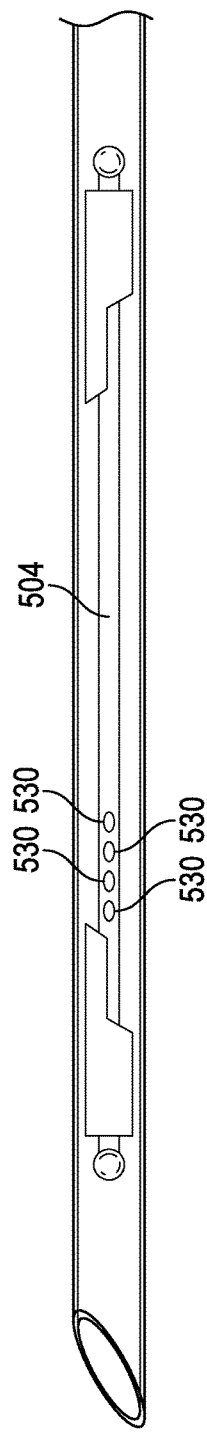
FIGS. 5(b)-5(c) show various stages of deployment of a multi-aperture embodiment of the invention.
Figure 5C:
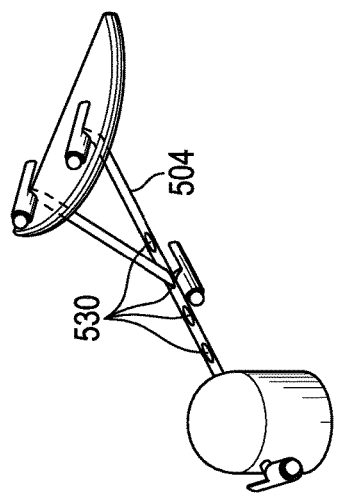

FIG. 5(a) shows a multi-chord embodiment of the invention. FIGS. 5(b)-5(c) show various stages of deployment of a multi-aperture embodiment of the invention.

FIG. 5(a) depicts an adjustable embodiment. The embodiment provides a similar delivery needle 502 to that shown in FIG. 2(b). Similar to FIG. 4(a), the prostheses of FIG. 5(a) is adjustable having chord 1 (504) and chord 2 (504') (which is longer than chord 1). The ramrod 503 or some similar actuation lever or arm still ejects the distal fluke 510 by abutting a shoulder or other such surface of the fluke. The embodiment includes two distal retention members 522, 523 respectively on chords 1 and 2 (e.g., knots, welds, couplers, heat fused joints). If chord 1 is not cut the retention member for chord 1 will abut the distal fluke and chord 1 may be deployed in tension when fully extended between the papillary muscle and leaflet. If chord 1 is cut then distal fluke may push the chord 1 retention member distally until the fluke abuts the retention member for chord 2 in addition to or instead of the retention member for chord 1. The distal knot/coupler 526 may allow chords 1 and 2 to pass through it or the distal knot/coupler may be removed in some embodiments. The embodiment includes two proximal retention members 524, 525 (e.g., knots, welds, couplers). If chord 1 is not cut the proximal retention member for chord 1 will abut the proximal fluke. If chord 1 is cut then proximal fluke 511 may push the chord 1 proximal retention member 527 proximally until the proximal fluke 511 abuts the proximal retention member for chord 2 instead of or in addition to the proximal retention member for chord 1. The proximal knot/coupler may allow chords 1 and 2 to pass through it or may be removed in some embodiments. Regardless of whether distal and proximal knot/couplers are included, chord 1 retainers 528 may be included in an embodiment such that if chord 1 is cut between the two chord 1 retainers then the chord 1 retainers (in cooperation with the distal and proximal chord 1 retention members) will prevent proximal and distal chord 1 remnants from escaping into the patient's heart/vascular system separate from the implant chord 2 because the chord 1 retainers and chord 1 retention members are sized to not pass through the flukes.

In the embodiment of FIG. 5(*a*) the distal retention members (collectively for chords 1 and 2) may be almost or entirely collinear with the chords 1 and 2 within the needle and the same is true for the proximal retention members for chords 1 and 2. This allows for differently sized chords that still maintain a minimal profile to fit within a small diameter needle (i.e., prevents excess slack for chord 2 from jamming within the needle).

In various embodiments the proximal and/or distal couplers may be sized to fit within the flukes (see proximal fluke) or be too large to do so (e.g., see distal fluke) or again, may be omitted altogether.

By trimming chord 1 the length of chord 2 will determine the overall chord length for the patient. If chord 1 is properly sized, chord 2 will remain but will not affect the function of the valve since the chord 1 will be the determining factor in terms of actual function/coupling papillary muscle to leaflet.

Thus, various embodiments (e.g., FIGS. 4(*a*) and 5(*a*)) include an adjustable artificial replacement chordae device/system for mitral valve repair. More specifically, an embodiment provides adjustable artificial replacement chordae that allow for variable chordal lengths encountered during valve repair surgery (e.g., mitral valve repair surgery). Such an embodiment allows for a more consistent and simple deployment of replacement chordae.

An embodiment (e.g., FIGS. 4(*a*) and 5(*a*)) allows for adjustment of the artificial chordae once surgically attached to the papillary muscle. The mechanisms of the embodiment are simple in that the surgeon is able to make adjustments simply by severing appropriate structures within the device which, as a result of the severing, extend the chordal length a prescribed amount. This contrasts with techniques where the surgeon must manually implant the device, check for proper length, adjust and repeat until proper coaptation has been achieved.

In FIGS. 5(*b*) and 5(*c*) embodiments each include a chord 504 with a plurality of apertures 530. The chord may be deployed in a manner similar to the system of FIG. 2(*b*). Afterword, other chords (such as those shown in FIGS. 1(*a*)-1(*f*)) may be coupled to and through any of the chord apertures (see FIG. 5(*c*))) to implant multiple chords into a leaflet with only a single chord traversing the papillary muscle.

Figure 6A:
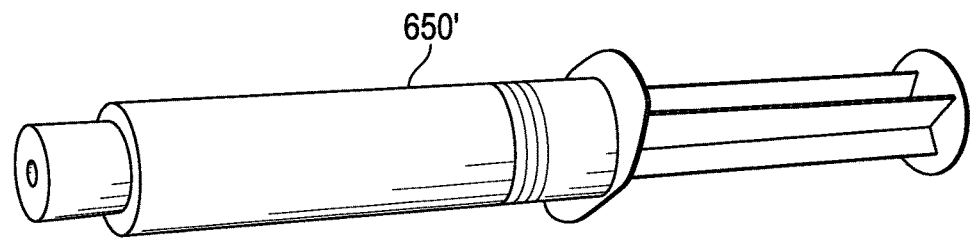
FIGS. 6(a)-6(c) illustrate various components of a kit in an embodiment of the invention.
Figure 6B:
Figure 6C:
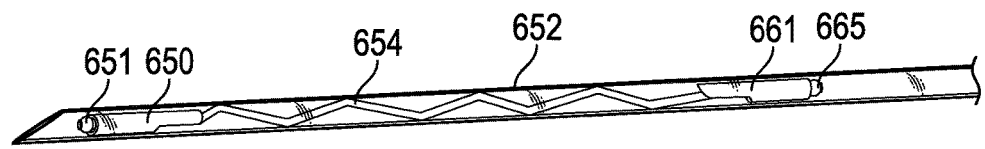
Figure 8A:
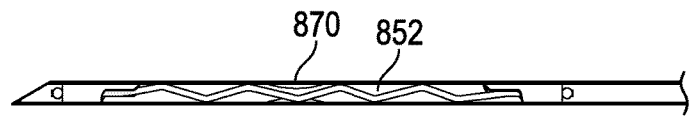
Figure 8B:
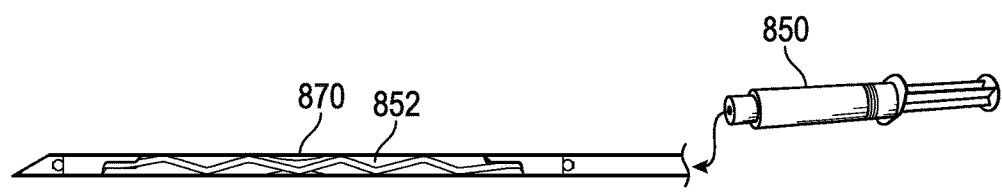
Figure 8C:
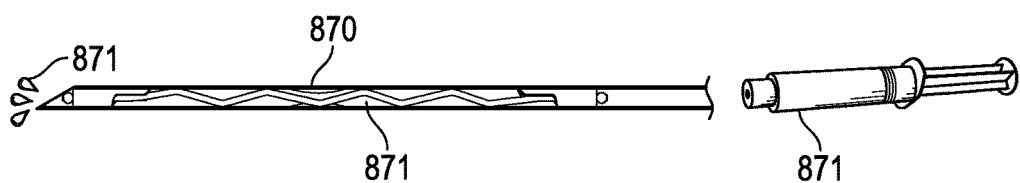
Figure 8D:
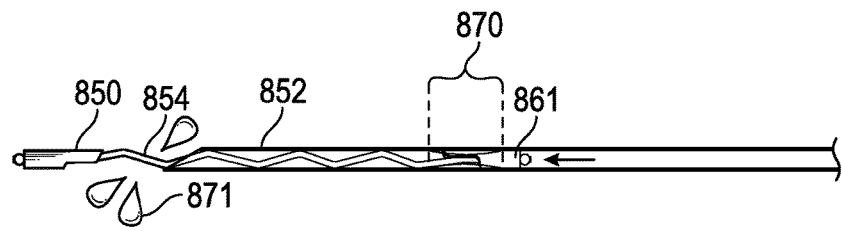

FIGS. 6(*a*)-6(*c*) illustrate various components of a kit in an embodiment of the invention. FIG. 6(*a*) includes syringe 650', FIG. 6(*b*) includes needle 652 housing a prosthesis with chord 654 and distal and proximal ferules 650, 661 that abut distal and proximal knots 651, 655. In an embodiment the prosthesis is preconfigured inside of long needle 652, and is packaged along with sterile saline syringes (e.g., syringe 650'). An embodiment includes a kit of between 3-5 needles and saline syringes (single use).

FIGS. 7(*a*)-7(*e*) illustrate various aspects of a crimped or compressed needle embodiment of the invention. In an embodiment approximately 0.25" from the needle tip, the needle is externally crushed over a precision gauge pin, resulting in a short crushed oval section 670. This oval shape presents a restriction to the circular fluke geometry. The implant is loaded into needle 652, and the proximal fluke 661 is forced past the oval section 670 while the distal fluke 650 is loaded into needle 652 before the oval section. FIGS. 7(*b*) and 7(*d*) each shows a side view of section 670 and FIG. 7(*c*) shows a top view of section 670. FIG. 7(*e*) shows one potential location for section 670 but other embodiments may include section 670 nearer either of flukes 650, 661.

FIGS. 8(*a*)-8(*g*) illustrate various stages of deployment of a crimped or compressed needle embodiment of the invention. The prosthesis is preloaded in the needle, ready for use (FIG. 8(*a*)). The syringe with sterile saline is then attached to the needle (FIG. 8(*b*)). The needle is primed with saline 871. With moderate saline pressure, distal fluke 850 is deployed. Proximal fluke 861 is obstructed by oval region 870 and will remain in the needle 852. In an embodiment, the proximal fluke 861 cannot be fully deployed with saline pressure. However, light tension on the suture 854 allows the entire prosthesis to be pulled from the needle (FIGS. 8(*d*)-8(*g*)).

A process for implanting a saline deployed embodiment is similar to that of FIGS. 3(*a*)-3(*f*). In an embodiment the surgeon measures the desired length for artificial chordae tendinae, and chooses a needle that is preconfigured with a prosthesis of corresponding length. A saline syringe is coupled with the selected needle, and the needle is primed with saline. In Step 1 the Surgeon pierces the mitral leaflet at the desired location (for chordal repair) with the needle. In Step 2 the surgeon pierces the papillary muscle at the desired location (for chordal repair) with the needle, and continues until the needle tip emerges on the far side of the papillary. In step 3 the surgeon applies moderate pressure to the syringe, which advances saline and deploys the distal end of the prosthesis at the far side of the papillary muscle. In step 4 the surgeon retracts the needle out of the papillary muscle. The fluke on distal end of the prosthesis engage (rotates into position) and secures the prosthesis onto the papillary. In step 5 the surgeon continues to retract the needle beyond the leaflet. Once the needle clears the leaflet, both syringe and needle can be discarded. In step 6 the surgeon tests valve coaptation with the prosthesis by pressurizing the ventricle with saline. The fluke on the proximal end of the prosthesis engage (rotates into position) and secures prosthesis onto leaflet (analogous to FIG. 3(*f*)). Surgeon may repeat the process if additional chords are desired.

An embodiment employs flukes (e.g., FIG. 3(*f*) with or without saline) to enable rapid system deployment. The flukes function like a grappling hook or similar coupling member. The fluke passes through cardiac tissue in a collapsed state (e.g., FIGS. 3(*c*)-(*d*) with or without saline) and then expands (e.g., rotates to position orthogonal with chord) on the far side of the tissue (e.g., FIGS. 3(*d*) and 3(*f*) with or without saline) to prevent the fluke and the chord attached thereto from backing out. This relieves the surgeon from manually knotting, crimping, and/or tying the prosthesis in place, which ultimately saves operation time.

In an embodiment the prosthesis is prefabricated and preloaded into the attachment device (deployment tube) (e.g., see FIG. 2(*b*) and FIG. 6(*b*)), which again relieves the burden on the surgeon from fabricating and/or loading the prosthesis at the table during surgery.

An embodiment includes a kit that includes multiple chords and deployment tubes in a variety of predetermined lengths, which will allow the surgeon to accurately achieve the correct geometry for that particular patient. This feature eliminates or reduces the variability that comes from a hand-tied prosthesis, and ultimately offers a more consistent product. In a related method, the surgeon may select several tubes to place several prostheses about a single leaflet or multiple leaflets. In such a case the surgeon may simply repeat the process in FIGS. 3(a)-3(f) (with or without saline) to implant more than one chord. The papillary muscle and leaflet are such that they can handle several "pokes" or penetrations by delivery needles to implant chordae, considering the relatively small diameter of the delivery needles. As a result, the surgeon has an "in-and-out technique" that capitalizes on simplicity and quickness and the ability to deploy 1 or more chordae. For example, three different "shots" or penetrations with delivery needles (to deploy 3 chordae) would be tolerable by papillary muscle and a leaflet.

In an embodiment the prosthesis that is implanted is comprised entirely of ePTFE and/or PTFE, which allows for excellent biocompatibility and tissue ingrowth into the construct. However, other embodiments use other materials for the chord (e.g., nylon) and the fluke of the prosthesis may be fabricated from a polymer or metal (e.g., Nitinol) that allows the fluke to collapse about the chord. Thus, for embodiments described herein as including ePTFE different versions of those same embodiments may include PTFE or other similar materials.

Furthermore, embodiments may provide materials with doping. For example, the ePTFE and/or PTFE materials described immediately above may be doped with, without limitation, Bismuth. The doping agent makes the implant ends radiopaque such that the surgeon can monitor the position of the implant during or after surgery.

As seen in FIG. 2(b), some embodiments include a long needle and a central ramrod which ejects the prosthesis. FIG. 2(a) includes a curved long needle and ramrod. FIG. 2(b) includes a straight long needle and ramrod. An embodiment includes a malleable needle which allows the surgeon to bend the needle to achieve the appropriate trajectory of the prosthesis, accounting for differing patient anatomy. In an embodiment the needle is flexible and will hold a bend such that the surgeon may position the needle in any orientation or angle to reach differing patient geometries (e.g., the malleable needle and ramrod may be formed into either of the configurations shown in FIGS. 2(a)-2(b)). In an embodiment the needle is a thin walled metal (e.g., stainless steel or Nitinol). In such an embodiment the ramrod is similarly a flexible component made of, for example, stainless steel, Nitinol, or a flexible polymer. However, other embodiments are not malleable and may be straight or curved.

While not shown, the ramrod of FIG. 2(b) may be thrust forward or distally by actuation of an actuation mechanism. Such an actuation device may take a number of forms including embodiments employing a scissor grip, pistol grip with trigger, wand with slider, syringe and plunger configuration, any of which can propel the ramrod forward to deploy a chord via one more clicks/actuations of the actuation mechanism.

An embodiment is used for mitral chordae Tendinae repair/replacement. However, other embodiments may be used in other surgical procedures where it is desirable to anchor two soft tissues together in a rapid manner (e.g., coupling tendon to muscle).

Regarding the surgical procedure, the orientation of the papillary muscle depends on the individual. Sometimes the muscle is in the base of the heart wall and rises up vertically like a water tower, on others it is on the side of the ventricle and juts out more horizontally. The surgeon may grab the tip of the muscle with forceps and manipulate the muscle to get the preferred orientation for surgery.

In an embodiment the system is a single use disposable attachment device containing a single prosthesis preloaded into the device. The system is delivered to the surgeon sterile.

An embodiment translates to a minimally invasive procedure (e.g., trans-catheter approach or through an intercostal space via transthoracic entry). Since conventional systems require additional instrumentation or surgeon intervention to secure the prosthesis, the conventional systems may have difficulty translating to minimally invasive or trans-catheter deployment. Conventional systems require an open approach and several instruments and components. In contrast, with an embodiment the surgeon inserts one device in to the patient's tissue, clicks the trigger (or flushes syringe), deploys the prosthesis, removes the delivery system, and the surgery is complete.

FIG. 4(a) depicts an adjustable embodiment. While the embodiment of FIG. 4(a) shows the longer and shorter cords joining at or near the knotted ends (or otherwise coupled ends), other embodiments may join the two chords more centrally such that the chords fuse or couple (e.g., by knot, bond, weld, etc.) just proximal to the distal fluke (fluke that abuts papillary muscle) and just distal to the proximal fluke (fluke that abuts leaflet) to ensure the fluke can achieve a small profile while loaded in a delivery needle. The embodiment may include no knot but instead couple the chords to each other with a weld, or the chords may be monolithic with each other where the couple is just a location where the cords couple to each other. For example, the chords may be cut or otherwise formed from a single piece of ePTFE.

Various embodiments have been described in conjunction with mitral valve repair but other uses are possible such as tricuspid valve repair or even suturing in locations apart from the heart. For example, there are orthopedic applications such as suturing connective tissue to bone. Specifically, a surgeon may anchor a loose ligament or tendon using an embodiment of the system. One end of the system is secured to the free end of the ligament, while the other is anchored in the bone. Based on range of motion desired in the joint, the surgeon then cuts prosthetic segments (e.g., the shorter chord of the adjustable embodiments of FIG. 4(a) and FIG. 5(a)) to achieve the correct length of tendon and the appropriate range of motion. In such a case the system may constitute a general anchoring or connective prosthesis.

In an embodiment a pledget may abut the distal fluke and/or proximal fluke to further dissipate stress in addition to the stress dissipation provided by the flukes. A pledget is to be interpreted as a buttress or shield to prevent, for example, a suture/coupling member from cutting tissue over time due to repetitive movement of the suture/coupling member. Some embodiments include no pledget. Some embodiments allow for a system to be shipped with no pledget but coupled to a pledget at a later time once the shipping container is opened and is ready for use by the surgeon.

In addition, materials are not restricted to ePTFE and/or PTFE and may include, for example (for the chords and/or flukes) silk, nylon, biodegradable materials (e.g., for suturing that is temporary in nature such as is the case with some orthopedic procedures) such as polyglycolic Acid (PGA), polylactic acid (PLA), poly(lactic-co-glycolic acid) (PLGA), polydioxanone (PDS), poly(orthoester) (POE), polycaprolactone (PCL), polymethylmethacrylate (PMMA), copolymer blends of the above, and the like. Other embodiments may include biological tissue for chord lengths. Also, the system need not be limited to just one material. For example, in the embodiments of Slide 3 the chords may be PTFE and the flukes may be ePTFE.

As used herein, a "fluke" includes objects like conduits or ferrules that pass the chord there through but then anchor the chord by preventing an end of the chord from passing through the fluke. A fluke, as used herein, is similar to a "treasury tag" or India tag used to fasten sheets of paper together or to a folder. Such a tag includes lace/chord with a tag (e.g., metal or ePTFE) at each end (where the ends are sharpened in some embodiments). The tags may be threaded through apertures in documents, tissue, and the like. The tag may be orthogonal to the lace upon deployment but in line with the lace while traversing an aperture. The tag may have a slot or aperture on one half of the cylinder that comprises the tag such that the lace may move from in-line with the tag to orthogonal to the tag (see FIG. 1(*e*)). The lace/chord may or may not be resilient. In an embodiment the first and second chords may include separate ePTFE strands joined together via heat (e.g., laser), weld, chemical reaction, and the like.

Knotless embodiments described herein improve device strength over current methods considering tying knots derates/lowers the strength of the base material (e.g., suture/chord). The knots introduce stress concentrations, which cause the knot to fail at a smaller load than the base material. Thus, eliminating/reducing the knots will improve the failure strength of the base material Embodiments described herein reduce variability over current methods. A current method of hand tying artificial chordae prosthetics out of ePTFE suture requires skill on the part of the surgeon. Each knot is comprised of between eight to ten throws in ePTFE suture. The knots could be tied incorrectly or the surgeon could miscount the requisite number of throws resulting in an inferior knot. By eliminating the knots altogether, an embodiment eliminates the variability that can be observed in the current method of hand tying artificial chordae prosthetics.

An embodiment reduces operating room (OR) time compared to current methods. Since the prosthetic is not fabricated during surgery, the duration that the patient is in surgery is reduced.

In an embodiment a staple or cinch may be coupled to the chord ends. Thus, instead of (or in addition to) heating the chord ends to couple the chords together (e.g., FIG. 4(*a*)) a cinch/staple/crimped metal sleeve may be attached to the distal chord ends.

Turning to FIGS. 6(*a*)-6(*c*), please note such an embodiment is suitable for a trans-catheter approach. For example, a needle (e.g., FIG. 6(*c*), a flexible needle, a jointed needle, conduit) may be advanced via transcutaneous catheter. The needle may couple to a fluid source, which may deploy the chord from the needle based on fluid pressure (e.g., from a plunger). Of course, other embodiments are not so limited and may include inserting the needle through a space between the patient's ribs.

The following examples pertain to further embodiments.

Example 1 includes an artificial chordae tendonae kit comprising: a hollow first needle including a first proximal end portion having a first proximal aperture, a first distal end portion having a first distal aperture, and a first middle portion coupling the first proximal end portion to the first distal end portion; a flexible first chord coupled to both a first proximal conduit and a first distal conduit; wherein the first proximal end portion includes a first proximal inner diameter directly adjacent the first proximal aperture, the first distal end portion includes a first distal inner diameter directly adjacent the first distal aperture, the first middle portion includes a first narrowed portion with a first middle inner diameter that is less than either of the first proximal inner diameter and the first distal inner diameter; wherein the first chord, the first proximal conduit, and the first distal conduit are all included within the first needle with the first distal conduit distal to the first narrowed portion and the first proximal conduit proximal to the first narrowed portion; wherein the first needle includes a long axis, the first chord includes a long axis, the first proximal conduit includes a long axis, and the first distal conduit includes a long axis; wherein the long axes of the first proximal and distal conduits are substantially parallel to the long axis of the first needle when the first chord is included within the first needle; wherein the first proximal and distal conduits are each configured to rotate when deployed from the first needle such that the long axes of the first proximal and distal conduits are each orthogonal to the long axis of the first chord when the first chord is fully extended into a linear orientation.

For instance, the proximal and distal conduits may include the flukes or ferrules 110, 111 of FIG. 1(*e*). For instance, in FIG. 7(*b*) the first middle inner diameter (e.g., dimension 681 (marked additionally at 683)) that is less than either of the first proximal inner diameter (e.g., 680) and the first distal inner diameter (e.g., 682). The dimensions are marked to outer diameters but assuming a consistent wall thickness, a person of ordinary skill in the art will understand the inner diameters would reflect the same relationships among each other as the outer diameters. Inner diameters are also marked at 683', 681' in FIG. 7(*d*). In FIGS. 1(*h*) and 2(*b*) the long axes of the first proximal and distal conduits (286, 284 respectively) are substantially parallel to the long axis of the first needle 285 when the first chord is included within the first needle. The first distal conduit is configured to rotate 286 when deployed from the first needle such that the long axis of the first distal conduit 284 is orthogonal to the long axis 288 of the first chord when the first chord is fully extended into a linear orientation (i.e., such as the "linear orientation" shown in FIG. 2(*b*) and not in FIG. 6(*c*)).

In example 2 the subject matter of the Example 1 can optionally include a hollow second needle including a second proximal end portion having a second proximal aperture, a second distal end portion having a second distal aperture, and a second middle portion coupling the second proximal end portion to the second distal end portion; a flexible second chord coupled to both a second proximal conduit and a second distal conduit; wherein the second proximal end portion includes a second proximal inner diameter directly adjacent the second proximal aperture, the second distal end portion includes a second distal inner diameter directly adjacent the second distal aperture, the second middle portion includes a second narrowed portion with a second middle inner diameter that is less than either of the second proximal inner diameter and the second distal inner diameter; wherein the second chord is included within the second needle with the second distal conduit distal to the second narrowed portion and the second proximal conduit proximal to the second narrowed portion; wherein the second needle includes a long axis, the second chord includes a long axis, the second proximal conduit includes a long axis, and the second distal conduit includes a long axis; wherein the long axes of the second proximal and distal conduits are substantially parallel to the long axis of the second needle when the second chord is included within the second needle; wherein the second proximal and distal conduits are each configured to rotate when deployed from the second needle such that the long axes of the second proximal and distal conduits are each orthogonal to the long axis of the second chord when the second chord is fully extended into a linear orientation; wherein first chord has a first length between its first proximal and distal conduits and the second chord has a second length between its second proximal and distal conduits substantially equal to the first length.

Regarding the second length being substantially equal to the first length, the kit may include similarly sized chords. However, the same kit may still have other chords of varying lengths and some kits may have only chords of varying lengths. Embodiments of kits accommodate varying anatomies and preferences of surgeons.

In example 3 the subject matter of the Examples 1-2 can optionally include a first proximal obstruction between the first proximal conduit and a proximal end of the first chord; and a first distal obstruction between the first distal conduit and a distal end of the first chord; wherein each of the first proximal and distal obstructions includes an outer diameter greater than an outer diameter of the first chord.

For example, the knots of FIG. 1(a) include such obstructions.

In example 4 the subject matter of the Examples 1-3 can optionally include wherein the first chord passes through the first distal conduit.

In example 5 the subject matter of the Examples 1-4 can optionally include wherein: the first distal conduit couples to a parabolic portion coupled to a proximal end of the first distal conduit; a first axis, orthogonal to the long axis of the first distal conduit, intersects two portions of the first distal conduit and the first chord; a second axis, orthogonal to the long axis of the first distal conduit, intersects only a single portion of the parabolic portion and the first chord.

Portion 289 of FIG. 1(h) constitutes an example of such a parabolic portion.

In example 6 the subject matter of the Examples 1-5 can optionally include the first chord passes through the first proximal conduit; the first proximal conduit couples to an additional parabolic portion coupled to a distal end of the first proximal conduit; an additional first axis, orthogonal to the long axis of the first proximal conduit, intersects two portions of the first proximal conduit and the first chord; and an additional second axis, orthogonal to the long axis of the first proximal conduit, intersects only a single portion of the additional parabolic portion and the first chord.

In example 7 the subject matter of the Examples 1-6 can optionally include a syringe configured to couple to the first proximal aperture of the first needle.

In example 8 the subject matter of the Examples 1-7 can optionally include wherein the first proximal conduit has an outer diameter that is greater than the first middle inner diameter.

For example, the outer diameter of the conduit would be greater than the inner diameter 683' of FIG. 7(d).

In example 9 the subject matter of the Examples 1-8 can optionally include wherein the first distal conduit has an outer diameter that is greater than the first middle inner diameter.

In example 10 the subject matter of the Examples 1-9 can optionally include wherein at least one of the first proximal and distal conduits are slidably coupled to the first chord.

For example, either or both of conduits of FIG. 2(b) may slide proximally and distally along the chord.

In example 11 the subject matter of the Examples 1-10 can optionally include wherein the first proximal conduit is deformable and configured to deform to slide past the first narrowed portion.

For example, the proximal conduit may be formed of polytetrafluoroethylene (PTFE) or expanded PTFE (ePTFE) and may deform or compress when passing the narrowed or compresses portion of the needle upon deployment.

In example 12 the subject matter of the Examples 1-11 can optionally include wherein the first chord includes a first chord material, the first proximal conduit includes a first proximal conduit material, and the first distal conduit includes a first distal conduit material that is the same as the first chord material and the first proximal conduit material.

In example 13 the subject matter of the Examples 1-12 can optionally include wherein the first distal conduit material includes polytetrafluoroethylene.

In example 14 the subject matter of the Examples 1-13 can optionally include wherein the first narrowed portion is included in a distal third of the first needle.

Figures 3A, 3B:
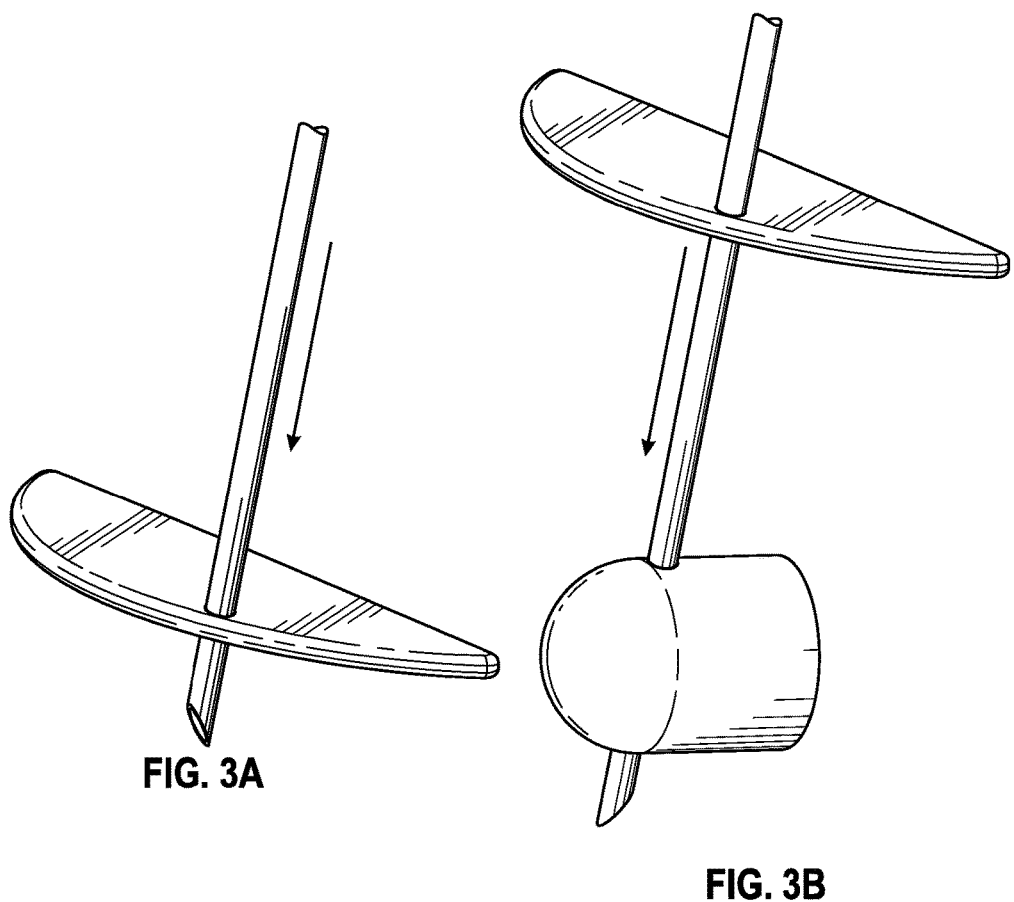
FIGS. 3(a)-3(f) show various stages of deployment in a process of an embodiment of the invention.
Figure 3C:
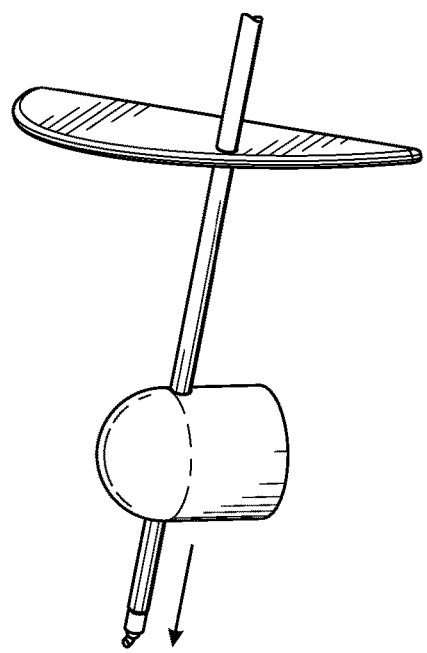
Figure 3D:
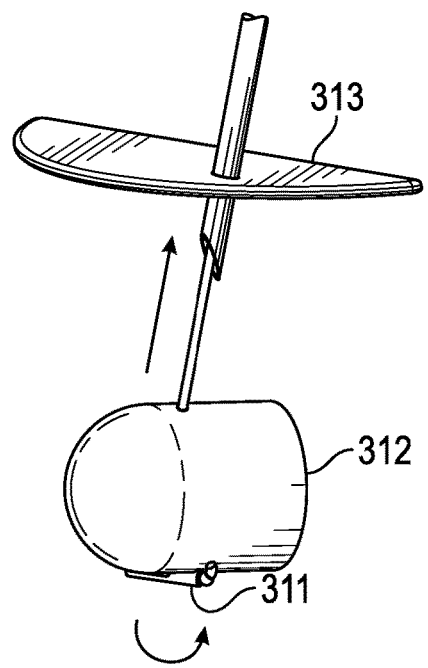
Figure 3E:
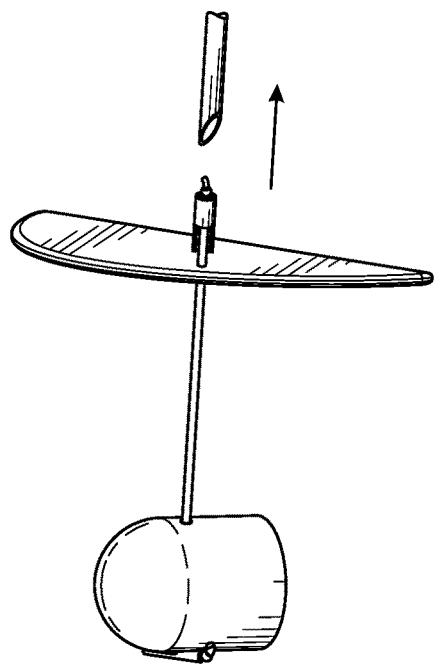
Figure 3F:
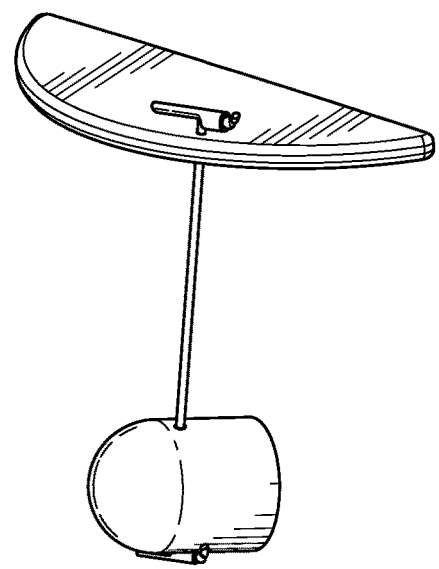

For instance, this positioning may be within 25 inches (6.35 mm) of the distal tip of the needle, such that the chord is within the needle for as long as possible and until the last moment when needle withdraws through the leaflet (e.g., FIG. 3(e)).

Example 15 includes an apparatus comprising: a hollow needle with a narrowed inner diameter in a distal third of the needle; and a flexible chord coupled to proximal and distal conduits; wherein the distal conduit is in the needle and distal to the narrowed inner diameter and the proximal conduit is in the needle and proximal to the narrowed inner diameter; wherein: (a)(i) long axes of the proximal and distal conduits are substantially parallel to a long axis of the needle when the proximal and distal conduits are in the needle, and (a)(ii) the proximal and distal conduits are configured to rotate when deployed from the needle such that their long axes are not parallel to a long axis of the chord when the chord is fully extended.

In example 16 the subject matter of the Example 15 can optionally include wherein: (b)(i) the chord passes through the proximal and distal conduits, and (b)(ii) the proximal conduit has an outer diameter that is greater than the narrowed inner diameter.

Example 17 includes an apparatus comprising: a hollow needle; and a flexible chord coupled to compressed proximal and distal anchors; wherein the chord and the proximal and distal anchors are in the needle; wherein the proximal and distal anchors: (a) are compressed when in the needle, and (b) decompressed when deployed from the needle such that each of their decompressed maximum outer diameters is greater than a maximum outer diameter of the needle.

The anchors may include ePTFE and/or PTFE, which can be compressed within the needle.

In example 18 the subject matter of the Example 17 can optionally include wherein the proximal and distal anchors each include a shape memory material.

For example, the shape memory material may include Nitinol. The Nitinol may be formed into a helical element that is generally linear in the needle (i.e., in a second shape that is linear and not helical) but resumes its primary state of a helical member once deployed from the needle. A pledget may be included adjacent the helical member so the pledget resides between the deployed helical member and the tissue (e.g., papillary muscle, mitral leaflet, or any other tissue). In another embodiment the shape memory material may be shape memory polymer (SMP), such as a polyurethane SMP. The SMP may have a glass transition temperature near 37-39 degrees Celsius so it resumes its primary "uncompressed" state once deployed from the needle and exposed to body temperature. A pledget may be included adjacent the SMP so the pledget resides between the deployed SMP and the tissue (e.g., papillary muscle, mitral leaflet, or any other tissue).

Example 19 includes a method comprising: providing a hollow needle, with a narrowed inner diameter in a distal third of the needle, and a flexible chord coupled to proximal and distal conduits; wherein (a)(i) the distal conduit is in the needle and distal to the narrowed inner diameter, and the proximal conduit is in the needle and proximal to the narrowed inner diameter; and (a)(ii) long axes of the proximal and distal conduits are substantially parallel to a long axis of the needle; traversing a mitral leaflet with the needle; traversing papillary muscle with the needle while still traversing the mitral leaflet with the needle; deploying the distal conduit from the needle and positioning the distal conduit against a first side of the papillary muscle; retracting the needle from the papillary muscle while leaving a portion of the chord traversing the papillary muscle from the first side of the papillary muscle to a second side of the papillary muscle; retracting the needle from the mitral leaflet while leaving an additional portion of the chord traversing the mitral leaflet from a first side of the mitral leaflet to a second side of the mitral leaflet; and deploying the proximal conduit from the needle and positioning the proximal conduit against the second side of the mitral leaflet.

In example 20 the subject matter of the Examples 19 can optionally include wherein deploying the distal and proximal conduits comprises rotating the distal and proximal conduits so their long axes are not parallel to a long axis of the chord when the chord is fully extended.

In example 21 the subject matter of the Examples 19-20 can optionally include wherein deploying the distal conduit comprises injecting a liquid into the needle to force the distal conduit out of the needle.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. An artificial chordae tendineae kit comprising:
a hollow first needle including a first proximal end portion having a first proximal aperture, a first distal end portion having a first distal aperture, and a first middle portion coupling the first proximal end portion to the first distal end portion;
a flexible first chord coupled to both a first proximal anchor and a first distal anchor;
wherein the first proximal end portion includes a first proximal inner diameter directly adjacent the first proximal aperture, the first distal end portion includes a first distal inner diameter directly adjacent the first distal aperture, the first middle portion includes a first narrowed portion with a first middle inner diameter that is less than either of the first proximal inner diameter and the first distal inner diameter;
wherein the first chord, the first proximal anchor, and the first distal anchor are all included within the first needle with the first distal anchor distal to the first narrowed portion and the first proximal anchor proximal to the first narrowed portion;
wherein the first needle includes a long axis, the first chord includes a long axis, the first proximal anchor includes a long axis, and the first distal anchor includes a long axis;
wherein the long axes of the first proximal and distal anchors are substantially parallel to the long axis of the first needle when the first chord is included within the first needle;
wherein the first proximal and distal anchors are each configured to rotate when deployed from the first needle such that the long axes of the first proximal and distal anchors are each nonparallel to the long axis of the first chord;
wherein the first proximal anchor is deformable and configured to deform to slide past the first narrowed portion.

2. The kit of claim 1 comprising:
a hollow second needle including a second proximal end portion having a second proximal aperture, a second distal end portion having a second distal aperture, and a second middle portion coupling the second proximal end portion to the second distal end portion;
a flexible second chord coupled to both a second proximal anchor and a second distal anchor;
wherein the second proximal end portion includes a second proximal inner diameter directly adjacent the second proximal aperture, the second distal end portion includes a second distal inner diameter directly adjacent the second distal aperture, the second middle portion includes a second narrowed portion with a second middle inner diameter that is less than either of the second proximal inner diameter and the second distal inner diameter;
wherein the second chord is included within the second needle with the second distal anchor distal to the second narrowed portion and the second proximal anchor proximal to the second narrowed portion;
wherein the second needle includes a long axis, the second chord includes a long axis, the second proximal anchor includes a long axis, and the second distal anchor includes a long axis;
wherein the long axes of the second proximal and distal anchors are substantially parallel to the long axis of the second needle when the second chord is included within the second needle;
wherein the second proximal and distal anchors are each configured to rotate when deployed from the second needle such that the long axes of the second proximal and distal anchors are each nonparallel to the long axis of the second chord;
wherein the first chord has a first length between its first proximal and distal anchors and the second chord has a second length between its second proximal and distal anchors substantially equal to the first length.

3. The kit of claim 1, comprising:
a first proximal obstruction between the first proximal anchor and a proximal end of the first chord; and
a first distal obstruction between the first distal anchor and a distal end of the first chord;

wherein each of the first proximal and distal obstructions includes an outer diameter greater than an outer diameter of the first chord.

4. The kit of claim 1, wherein the first chord passes through the first distal anchor.

5. The kit of claim 4, wherein:
the first distal anchor couples to a parabolic portion coupled to a proximal end of the first distal anchor;
a first axis, orthogonal to the long axis of the first distal anchor, intersects two portions of the first distal anchor and the first chord;
a second axis, orthogonal to the long axis of the first distal anchor, intersects only a single portion of the parabolic portion and the first chord.

6. The kit of claim 5, wherein:
the first chord passes through the first proximal anchor;
the first proximal anchor couples to an additional parabolic portion coupled to a distal end of the first proximal anchor;
an additional first axis, orthogonal to the long axis of the first proximal anchor, intersects two portions of the first proximal anchor and the first chord; and
an additional second axis, orthogonal to the long axis of the first proximal anchor, intersects only a single portion of the additional parabolic portion and the first chord.

7. The kit of claim 1 comprising a syringe configured to couple to the first proximal aperture of the first needle.

8. The kit of claim 1, wherein the first proximal anchor has an outer diameter that is greater than the first middle inner diameter.

9. The kit of claim 1, wherein the first distal anchor has an outer diameter that is greater than the first middle inner diameter.

10. The kit of claim 1, wherein at least one of the first proximal and distal anchors are slidably coupled to the first chord.

11. The kit of claim 1, wherein the first chord includes a first chord material, the first proximal anchor includes a first proximal anchor material, and the first distal anchor includes a first distal anchor material that is the same as the first chord material and the first proximal anchor material.

12. The kit of claim 11, wherein the first distal anchor material includes polytetrafluoroethylene.

13. The kit of claim 1, wherein the first narrowed portion is included in a distal third of the first needle.

14. An apparatus comprising: a hollow needle with a narrowed inner diameter in a distal third of the needle; and a flexible chord coupled to proximal and distal anchors; wherein the distal anchor is in the needle and distal to the narrowed inner diameter and the proximal anchor is in the needle and proximal to the narrowed inner diameter; wherein: (a)(i) long axes of the proximal and distal anchors are substantially parallel to a long axis of the needle when the proximal and distal anchors are in the needle, (a)(ii) the proximal and distal anchors are configured to rotate when deployed from the needle such that their long axes are not parallel to a long axis of the chord; and (a)(iii) the proximal anchor is deformable and configured to deform to slide past the narrowed inner diameter.

15. The apparatus of claim 14, wherein: (b)(i) the chord passes through the proximal and distal anchors, and (b)(ii) the proximal anchor has an outer diameter that is greater than the narrowed inner diameter.

16. The apparatus of claim 14, wherein the proximal and distal anchors each include a shape memory material.

17. The apparatus of claim 14, wherein the proximal and distal anchors include proximal and distal conduits.

18. A method comprising:
providing a hollow needle, with a narrowed inner diameter in a distal third of the needle, and a flexible chord coupled to proximal and distal anchors; wherein (a)(i) the distal anchor is in the needle and distal to the narrowed inner diameter, and the proximal anchor is in the needle and proximal to the narrowed inner diameter; and (a)(ii) long axes of the proximal and distal anchors are substantially parallel to a long axis of the needle;
traversing a mitral leaflet with the needle;
traversing papillary muscle with the needle while still traversing the mitral leaflet with the needle;
deploying the distal anchor from the needle and positioning the distal anchor against a first side of the papillary muscle;
retracting the needle from the papillary muscle while leaving a portion of the chord traversing the papillary muscle from the first side of the papillary muscle to a second side of the papillary muscle;
retracting the needle from the mitral leaflet while leaving an additional portion of the chord traversing the mitral leaflet from a first side of the mitral leaflet to a second side of the mitral leaflet; and
deploying the proximal anchor from the needle and positioning the proximal anchor against the second side of the mitral leaflet;
wherein the proximal anchor is deformable and configured to deform to slide past the narrowed inner diameter.

19. The method of claim 18, wherein deploying the distal and proximal anchors comprises rotating the distal and proximal anchors so their long axes are not parallel to a long axis of the chord.

20. The method of claim 18, wherein deploying the distal anchor comprises injecting a liquid into the needle to force the distal anchor out of the needle.

* * * * *